United States Patent [19]

Eley et al.

[11] Patent Number: 5,665,381
[45] Date of Patent: Sep. 9, 1997

[54] INHIBITION OF AGGREGATION OF DRUG CONTAINING PARTICLES

[75] Inventors: Crispin G. S. Eley, Fullerton; Eric A. Forssen, LaCañada, both of Calif.

[73] Assignee: NeXstar Pharmaceuticals, Inc., Boulder, Colo.

[21] Appl. No.: 472,001

[22] Filed: Jun. 6, 1995

Related U.S. Application Data

[63] Continuation of Ser. No. 820,610, Feb. 25, 1992, abandoned.
[51] Int. Cl.$^6$ .................................................. A61K 9/133
[52] U.S. Cl. ...................... 424/450; 264/4.3; 264/4.6
[58] Field of Search ........................... 264/4.3, 4.32, 264/4.6; 424/450; 436/829

[56] References Cited

U.S. PATENT DOCUMENTS

| | | | |
|---|---|---|---|
| 3,993,754 | 11/1976 | Rahman et al. | 424/450 |
| 4,078,052 | 3/1978 | Papahadjopoulos | 424/450 |
| 4,622,294 | 11/1986 | Kung et al. | 436/829 X |
| 4,708,861 | 11/1987 | Popescu et al. | 264/4.32 X |
| 4,721,612 | 1/1988 | Janoff et al. | 424/450 X |
| 4,762,720 | 8/1988 | Jizomoto | 424/450 |
| 4,762,915 | 8/1988 | Kung et al. | 424/450 X |
| 4,769,250 | 9/1988 | Forssen | 424/450 |
| 4,873,035 | 10/1989 | Wong | 264/4.6 |
| 4,946,683 | 8/1990 | Forssen | 424/450 X |
| 4,975,282 | 12/1990 | Cullis et al. | 424/450 |
| 5,192,549 | 3/1993 | Barenholtz et al. | 424/450 |

OTHER PUBLICATIONS

Liposomes: Preparation, Charcterization, and Preservation, Lightenberg and Barenholz, Methods Biochemical Anaysis 33:439–441 (1988) published in "Methods of Biochemical Analysis", David Glick, John Wiley & Sons, pp. 440 paragraph 3.
PCT/US 92/01083 20 Nov. 1992 Search Report.
CA 117(18): 173704v, Domard et al., FR 2667072 (Mar. 1992).
CA115(11): 109926a, Bakas et al., Cryobiology, 28(3) 279–87 (1991).
CA 114(5):38083q, Kaszuba et al., J. Inorg. Biochem., 40(3), 217–25 (1990).

*Primary Examiner*—Richard D. Lovering
*Attorney, Agent, or Firm*—NeXstar Pharmaceuticals, Inc.

[57] ABSTRACT

A method and composition for the prevention of aggregation of liposomes which include a multivalent anion disposed on the outer surface thereof comprises the addition of a divalent cation to the external aqueous phase.

7 Claims, No Drawings

INHIBITION OF AGGREGATION OF DRUG CONTAINING PARTICLES

The present application is a Rule 1.60 continuation application of U.S. Ser. No. 07/820,610, filed Feb. 25, 1992 now abandoned.

FIELD OF THE INVENTION

This invention relates to the field of biochemistry and medicine, and more particularly to a method of preventing aggregation and fusion in pharmaceutical preparations which include particle-associated multivalent anionic moieties.

BACKGROUND AND SUMMARY OF THE INVENTION

Liposomes, also known as phospholipid vesicles, are known to be physiologically compatible particles which provide biodegradable delivery systems for a broad range of drugs. For example, U.S. Pat. No. 5,019,369 teaches a method of targeting diagnostic and chemotherapeutic agents to tumors in the body of a patient by the intravenous administration of the agent encapsulated in unilamellar liposomes having a diameter of less than 200 nm.

Liposomes are microscopic delivery vesicles which are comprised of phospholipids which are polar molecules having a hydrophilic (ionizable) headgroup, and a hydrophobic tail consisting of fatty acid chains. Phospholipids form dosed, fluid filled spheres when properly mixed with water. The hydrophobic tails spontaneously associate and exclude the water, while the hydrophilic phosphate ester headgroups are preferentially positioned toward the water.

The result is a spherical bilayer membrane in which the fatty acid tails point towards the interior of the membrane, and the polar heads point toward the aqueous medium. The polar heads at the inner surface of the membrane point toward the liposome's aqueous interior and those at the other (outer) surface point toward the exterior aqueous medium (i.e., the external continuous phase of the liposome dispersion). Liposomes may be either multilamellar, like an onion, with liquid separating many lipid bilayers, or unilamellar, with a single bilayer surrounding a liquid center. Finely divided phospholipids dispersed in aqueous solution spontaneously form bilayers, and simple agitation of the mixture usually produces multilamellar vesicles (MLVs), structures having diameters of 1–10 μm (1000–10,000 nm). Sonication of these structures, or other methods known in the art, leads to formation of unilamellar vesicles (UVs) having an average diameter of about 30–200 nm. The actual equilibrium diameter is largely determined by the nature of the phospholipid used, the suspending buffer, and the extent of incorporation of other lipids such as cholesterol. Standard methods for the formation of liposomes are known in the art, for example, methods for the commercial production of liposomes are described in U.S. Pat. No. 4,753,788 to Ronald C. Gamble and U.S. Pat. No. 4,935,171 to Kevin R. Bracken, the disclosures of which are incorporated herein by reference.

Liposomes for use in the invention can be prepared by any of the techniques now known in the art or subsequently developed. For example, the liposomes can be formed by the conventional technique for preparing MLVs, that is, by depositing a selected lipid on the inside wall of a suitable vesicle by dissolving the lipid in chloroform, and then evaporating the dissolvent to leave a thin film on the inside of the vessel. An aqueous solution is then added to the vessel with a swirling or vortexing motion which results in the formation of large multilamellar vesicles.

Unilamellar vesicles can be prepared by reverse phase evaporation, infusion procedures, detergent dilution and sonication, that is, by providing a shear force necessary to form the smaller, unilamellar vesicles.

In addition to liposomes, other lipid particles such as those described in U.S. Pat. No. 4,963,363 or other particles may be maintained for extended periods in a non-aggregative form, when the described anions are present on the outer surface of the particle according to the process of this invention.

It is also known to load liposomes with cationic, lipophilic drags by first forming the liposomes in an aqueous medium in the presence of an organic acid which has multiple ionizable functional groups, and exchanging the unentrapped solution for a more basic (i.e., a solution having a higher pH) solution and adding a drug to the dispersion to load the drug into the liposomes. See, for example, U.S. Pat. No. 4,946,683 to Forssen.

However, there may be potential problems with certain liposome dispersions, particularly those containing smaller liposomes or liposomes which include a multivalent anion disposed on the surface, in that vesicle aggregation or flocculation may occur upon prolonged storage in liquid form.

Accordingly, it has been a desideratum to provide a facile way to assure that aggregation of liposomes does not occur, thus extending the shell life and optimizing the production of liposomes.

The present invention provides a method for the prevention of aggregation of lipid particles (e.g., liposomes) which are dispersed in an external aqueous medium (i.e., a continuous phase) and which include a multivalent anion, the method comprising the inclusion of a divalent cation in the continuous phase. Preferably, the divalent cation is selected from the group consisting of calcium and magnesium. In terms of the relative amounts of cation and lipids which are present in the dispersion, the divalent cation is present in an mount of up to 1.5:1 mole ratio with respect to total lipid content, preferably 0.002:1 to 0.9:1, most preferably 0.002:1 to 0.6:1. For most formulations, the divalent cation may be present in the continuous phase of the liposome dispersions in an mount of up to 50 mM, preferably 0.1 to 25 mM and most preferably from 0.1 to 16 mM to provide a reliable working range. While in the examples which follow the cation is added to the liposome dispersion, in other formulations the cation might be added to the hydrating buffer solution prior to liposome formation and have a similar anti-aggregative effect if the metal ion remains present in the external phase.

The divalent cation is added to the dispersion in the form of a salt, most preferably a salt selected from the group consisting chloride, bromide, iodide, nitrate, nitrite or carbonate. Most preferably, the divalent cation is calcium and is in the form of a soluble salt.

The multivalent anion of the liposome is selected from the group consisting of citrate, succinate, tartrate, oxalate, isocitrate, glutarate, fumarate, maleate, malonate, adipate, phthalate and dextran sulfate. The multivalent anion is usually found on the liposome in residual form, e.g., adhering to the liposome following a buffer replacement. The residual multivalent anion is thought to be a principal cause of aggregation in such liposomes.

DETAILED DESCRIPTION OF THE INVENTION

Biological lipids from which liposomal bilayer membrane particles or vesicles useful in practicing this invention can be prepared are amphiphilic (containing both a hydrophobic and hydrophilic portion) molecules which can spontaneously aggregate to form small spheres, ellipsoids or long cylinders, or bilayers having two or more parallel layers of amphiphilic molecules. In an aqueous (polar) medium, the polar heads of the amphiphilic molecules making up one layer orient outwardly to extend into the surrounding medium while the non-polar tail portions of these molecules likewise associate with each other. This provides a polar surface and a non-polar core in the wall of the vesicle. Such bilayered micelles usually take the shape of unilamellar (having one bilayer) or multilamellar (having a plurality of substantially concentric bilayers) spherical vesicles having an internal aqueous compartment.

Liposome bilayer membrane particles which have been found to be suitable in practicing this invention are small unilamellar vesicles having a mean diameter of from 30 to 150 nanometers (nm), and preferably from about 45 to about 60 nm, which are neutral (uncharged or having balanced charges; i.e., zwitterions) to induce specificity and tissue/cell targeting, thereby maximizing uptake of the resulting liposome drug delivery system.

Such liposome bilayer membrane particles include ones made from dipalmitoylphosphatidylcholine, distearoylphosphatidylcholine, dioleoylphosphatidylethanolamine, distearoylphosphatidylserine, dilinoleoylphosphatidylinositol, distearoylphosphatidylglycerol, and the like, or mixtures thereof. Liposome bilayer membrane particles made entirely from neutral phospholipids, such as distearoylphosphatidylcholine, and preferably ones which have been further stabilized with cholesterol or like-acting substances, for example in a molar ratio of distearoylphosphatidylcholine:cholesterol of about 2:1, respectively, have been found to be particularly suitable with regard to targeting efficiency when used to deliver anthracycline antineoplastic agents.

The invention is especially useful in preventing aggregation of particles containing cationic, ionizable lipophilic drugs, e.g., dibucaine, pilocarpine, quinine, prodipine, timolol, pentamidine, benadryl, dopamine, epinephrine, codeine, morphine, atropine, imipramine, quinidine, chloropromazine, and specifically anthracycline compounds having antineoplastic activity against cancerous tissues or cells, including daunorubicin, doxorubicin, mitoxantrone, aclacinomycin A, vinblastine, vincristine and mitomycin C.

While the particular type of particle, type and ratios of the included lipids, type of encapsulated drug and the various process parameters may affect the behavior and effect of the particle in several ways, for example, the ability of the particle to properly encapsulate bioactive agents, the operative factors which enable the practice of this invention are the presence of the described residual multivalent anions on the external surface of the particles, and the inclusion of the described divalent cation in the external phase of the particle dispersion.

In the examples which follow, liposomes are first formed by hydrating a dried lipid film or powder in an aqueous solution which includes a multivalent anion, preferably an organic add anion. The acidity of the anion buffer solution may be add or dose to neutral pH, depending on the process employed for loading the drug.

The dispersion of lipids in the hydrating buffer is then homogenized in a modified Gaulin homogenizer (according to the method described in U.S. Pat. No. 4,753,788) until liposomes of the appropriate size are formed. In general, the liposomes are heated during the homogenization step to a temperature that exceeds the transition temperature of the lipids which are employed. The drug is then added, under conditions which are specific to the particular method, and loaded into the liposomes. The divalent cation may be introduced at this step.

Preferably, the liposome dispersion is then ultrafiltered and washed with a buffer that contains the divalent cation. The liposomes are then sterile filtered.

Example 1 provides a description of liposomes which are loaded with daunorubicin by an ionic loading procedure. This procedure is described in the patent application PCT/US91/04807, filed Jul. 3, 1991 and incorporated herein by reference.

EXAMPLE 1

A mixture of chemically pure distearoyl phosphatidylcholine and cholesterol was dissolved in a 2:1 molar ratio in a chloroform/methanol solution. This solution was then dried to form a finely divided powder. The lipid powder was then hydrated in a buffer comprising 125 mM sucrose, 50 mM citric acid and 125 mM ethylenediamine at a pH of 7.5, at 65° to 72° C. for one hour. This dispersion was then homogenized in the modified Gaulin homogenizer (according to the method described in U.S. Pat. No. 4,753, 788) at 10,000 psi. This procedure formed small unilamellar vesicles, which were then filtered through a 0.8 μm AAWP Millipore filter membrane at 65° C.

The liposome dispersion was then ultrafiltered in a Millipore Minitan tangential flow ultrafilter (with 100,000 nominal molecular weight limit [NMWL] polysulfone filters) with a wash buffer containing 250 mM sucrose and 50 mM glycine, to remove the external (unentrapped) citric acid and ethylenediamine.

The ultrafiltered liposomes were loaded by first heating the empty vesicles to 65° C. Daunorubicin hydrochloride was then added to the dispersion at a 17.4 to 1 lipid to drug ratio. The pH of the continuous phase was then adjusted to 7.5 with various combinations of base and/or calcium salt (as listed in the Table) to maintain a pH equal to that of the internal phase, and the dispersion was incubated at 65° C. for 15 minutes. The dispersion was then allowed to cool to room temperature and the stability to aggregation was determined.

EXAMPLE 2

The procedure of Example 1 was followed in which the pH of the continuous phase was adjusted either by the addition of a combination of sodium hydroxide and calcium chloride to yield a final continuous phase calcium chloride concentration of 2 mM, or by sodium hydroxide alone. The liposomal drug dispersion was then ultrafiltered with the addition of calcium ions, according to the method of the invention, for the calcium chloride containing sample. First, the dispersion of daunorubicin containing liposomes was diluted 1:3 with a wash buffer which included 250 nM sucrose, 50 mM glycine and 2 mM calcium chloride. The dispersion was then ultrafiltered, in the 100,000 NMWL Minitan for a period of time sufficient to provide a one volume wash with the sucrose/glycine/cation wash buffer. The buffer influx was then temporarily stopped to concentrate the dispersion to 2.5 mg daunorubicin per ml. The ultrafiltration was then continued with the wash buffer until the conductivity of the chute was reduced to the base line of the original wash buffer, i.e., about 360 micro MHO. The liposome dispersion was then sterile filtered to provide an aseptic therapeutic liposomal daunorubicin formulation. The liposomal sample pH adjusted without calcium chloride present, was similarly processed using the same wash buffer without calcium chloride. Sample stability to aggregation was then determined and results are shown in the Table.

EXAMPLE 3

Liposomes were loaded with daunorubicin according to the method described in U.S. Pat. No. 4,946,683, the disclosure of which is incorporated herein by reference. A dried lipid powder comprising 2:1 DSPC:cholesterol was added to a hydrating buffer comprising 125 mM sucrose and a 50 mM citric acid (buffer pH 2.2) at 50° C. and held for 3 minutes.

This dispersion of lipids was then homogenized in a modified Gaulin homogenizer, described in U.S. Pat. No. 4,946,683, at 10.2K psi to produce unilamellar vesicles having a diameter of from 40 to 90 nm. Daunorubicin was loaded into these vesicles by first heating the vesicles in the hydrating buffer to 55° C., adding 3 grams per liter daunorubicin hydrochloride, adjusting the pH of the external (continuous) phase to 6.28 with either sodium hydroxide or sodium bicarbonate, and incubating the dispersion at 55° C. for 20 minutes.

This dispersion of drug-loaded liposomes was then 0.8 μm filtered at 55° C. and the pH was adjusted with 2.5M HCl to pH 5.3.

The liposome dispersion was ultrafiltered, with the addition of a divalent cation according to the method of the invention. First, the dispersion of daunorubicin containing liposomes was diluted 1:3 with a wash buffer which included 250 mM sucrose, 50 mM glycine and one of several salts set forth below in the Table. The salts were added in varying amounts up to 20 mM. The dispersion was then ultrafiltered, in the 100,000 NMWL Minitan for a period of time sufficient to provide a one volume wash with the sucrose/glycine/cation wash buffer. The make up buffer flow was then temporarily stopped to concentrate the dispersion to 2.5 mg daunorubicin per ml. The ultrafiltration was then continued with the wash buffer until the conductivity of the eluate was reduced to the base line of the original wash buffer, i.e., about 360 micro MHO. The liposome dispersion was then filtered through a 0.2 μm membrane to provide an aseptic therapeutic liposomal daunorubicin formulation.

The advantages of the invention are shown by the Table. The presence of the divalent cations calcium and magnesium, in amounts of up to 40 mM (0.74 to 1 mole ratio cation to lipid) inhibits the aggregation of the liposomes. As used herein, aggregation in a liposome dispersion is determined by the presence or formation of visible particulates in the dispersion or by an increase in solution turbidity. Experiments have also been performed with lipid concentrations which were 50% of several of those in the above Examples, i.e., at cation to lipid ratios two fold higher than those in the Table. Similar results were shown with respect to the inhibition of aggregation.

From the foregoing description the essential characteristics of the invention can be readily ascertained and, without departing from the spirit and scope thereof, the invention can be adapted to various usages. Changes in form and the substitution of equivalents are contemplated as circumstances may suggest or render expedient, in the context of the following claims.

TABLE

| | Final concentration of Cation in the External Phase of the Liposome Dispersion | | | | |
|---|---|---|---|---|---|
| | | mole ratio | Aggregation | | |
| Ex. | mM | cation/lipid | day 1 | day 7 | day 115 |
| 1 | none | 0 | yes | — | — |
| 1 | 1 mM CaCO$_3$ | 0.019:1 | none | — | — |
| 1 | 5 mM CaCO$_3$ | 0.093:1 | none | — | — |
| 1 | 10 mM CaCO$_3$ | 0.185:1 | none | — | — |
| 1 | 40 mM CaCO$_3$ | 0.741:1 | none | — | — |
| 1 | 1.25 mM NaHCO$_3$ | 0.023:1 | yes | — | — |
| 1 | 2.5 mM NaHCO$_3$ | 0.046:1 | yes | — | — |
| 1 | 5 mM NaHCO$_3$ | 0.093:1 | yes | — | — |
| 1 | 6.5 mM NaHCO$_3$ | 0.120:1 | yes | — | — |
| 1 | 12.5 mM NaHCO$_3$ | 0.231:1 | yes | — | — |

TABLE-continued

| | Final concentration of Cation in the External Phase of the Liposome Dispersion | | | | |
|---|---|---|---|---|---|
| | | mole ratio | Aggregation | | |
| Ex. | mM | cation/lipid | day 1 | day 7 | day 115 |
| 1 | 0 mM CaCl$_2$** | 0 | slight* | — | — |
| 1 | 1 mM CaCl$_2$ | 0.019:1 | none | — | — |
| 1 | 2 mM CaCl$_2$** | 0.037:1 | none | — | — |
| 1 | 5 mM CaCl$_2$** | 0.093:1 | none | — | — |
| 1 | 10 mM CaCl$_2$** | 0.185:1 | none | — | — |
| 1 | 40 mM CaCl$_2$** | 0.741:1 | none | — | — |
| 1 | 2 mM Ca(NO$_3$)$_2$** | 0.037:1 | none | — | — |
| 1 | 3 mM Ca(OH)$_2$ | 0.055:1 | none | — | — |
| 1 | 16 mM CaCl$_2$ | 0.296:1 | none | — | — |
| 3 | 1 mM CaCl$_2$ | 0.019:1 | none | none | none |
| 2,3 | 2 mM CaCl$_2$ | 0.037.1 | none | none | none |
| 3 | 3 mM CaCl$_2$ | 0.055:1 | none | none | none |
| 3 | 4 mM CaCl$_2$ | 0.074:1 | none | none | none |
| 3 | 7 mM CaCl$_2$ | 0.129:1 | none | none | none |
| 3 | 2 mM MgCl$_2$ | 0.037:1 | none | yes | — |
| 3 | 2 mM ZnCl$_2$ | 0.037:1 | yes | — | — |
| 3 | 2 mM NaCl | 0.037:1 | yes | — | — |
| 3 | 4 mM NaCl | 0.074:1 | yes | — | — |
| 2 | none | 0 | yes | — | — |

*slight trace of aggregation, and aggregated on day 2.
**pH adjusted with NaOH
— indicates that the test was not continued through this time period.

I claim:

1. A method for inhibiting aggregation of unilamellar liposomes containing an encapsulated drug and containing residual amounts of multivalent anions disposed on the outer surface of said liposomes, comprising (a) forming a dispersion of unilamellar liposomes containing an encapsulated drug wherein residual amounts of a multivalent anion are disposed on the outer surface of said liposomes; and (b) adding to said dispersion an effective amount to inhibit aggregation of a divalent cation selected from the group consisting of calcium and magnesium; wherein the liposomes have a mean diameter less than 200 nm and would otherwise aggregate in the absence of the divalent cation.

2. The method of claim 1, in which the multivalent anion is selected from the group consisting of citrate, succinate, tartrate, oxalate, isocitrate, glutarate, fumarate, maleate, malonate, adipate, phthalate and sulfate.

3. The method of claim 1 or 2 in which the divalent cation is calcium.

4. The method of claim 3 which the liposomes are comprised of lipids and the divalent cation is present in the aqueous medium in an amount of up to 1.5:1 mole ratio with respect to total lipid content of the liposomes.

5. The method of claim 3 in which the liposomes are comprised of lipids and the divalent cation is present in the aqueous medium in a mole ratio of from 0.002:1 to 0.9:1 with respect to total lipid content of the liposomes.

6. The method of claim 1 or 2 in which the liposomes are comprised of lipids and the divalent cation is present in the aqueous medium in an amount of up to 1.5:1 mole ratio with respect to total lipid content of the liposomes.

7. The method of claim 1 or 2 in which the liposomes are comprised of lipids and the divalent cation is present in the aqueous medium in a mole ratio of from 0.002:1 to 0.9:1 with respect to total lipid content of the liposomes.

* * * * *